(12) United States Patent
Stone et al.

(10) Patent No.: US 11,236,125 B2
(45) Date of Patent: Feb. 1, 2022

(54) MIXED BED ION EXCHANGE ADSORBER

(71) Applicant: EMD Millipore Corporation, Burlington, MA (US)

(72) Inventors: Matthew T. Stone, Burlington, MA (US); John P. Amara, Burlington, MA (US)

(73) Assignee: EMD Millipore Corporation, Burlington, MA (US)

( * ) Notice: Subject to any disclaimer, the term of this patent is extended or adjusted under 35 U.S.C. 154(b) by 53 days.

(21) Appl. No.: 16/561,453

(22) Filed: Sep. 5, 2019

(65) Prior Publication Data

US 2019/0389901 A1 Dec. 26, 2019

Related U.S. Application Data

(62) Division of application No. 15/521,428, filed as application No. PCT/US2015/053140 on Sep. 30, 2015, now abandoned.

(60) Provisional application No. 62/089,030, filed on Dec. 8, 2014.

(51) Int. Cl.
| | |
|---|---|
| *C07K 1/20* | (2006.01) |
| *C07K 1/18* | (2006.01) |
| *C07K 1/36* | (2006.01) |
| *B01D 15/38* | (2006.01) |
| *B01D 63/02* | (2006.01) |

(52) U.S. Cl.
CPC ............ *C07K 1/20* (2013.01); *B01D 15/3804* (2013.01); *B01D 63/02* (2013.01); *C07K 1/18* (2013.01); *C07K 1/36* (2013.01); *B01D 2311/2626* (2013.01)

(58) Field of Classification Search
CPC ... C07K 1/20; C07K 1/36; C07K 1/18; B01D 15/3804; B01D 63/02; B01D 2311/2626
See application file for complete search history.

(56) References Cited

U.S. PATENT DOCUMENTS

| | | |
|---|---|---|
| 3,382,305 A | 5/1968 | Breen |
| 3,936,394 A | 2/1976 | Kusunose et al. |
| 4,169,790 A | 10/1979 | Pretorius et al. |

(Continued)

FOREIGN PATENT DOCUMENTS

| | | |
|---|---|---|
| CN | 2455356 Y | 10/2001 |
| CN | 1807465 A | 7/2006 |

(Continued)

OTHER PUBLICATIONS

International Search Report and Written Opinion dated Apr. 6, 2012 in co-pending PCT application No. PCT/JS2011/045519.

(Continued)

*Primary Examiner* — Krishnan S Menon
(74) *Attorney, Agent, or Firm* — Nields, Lemack & Frame, LLC (57) ABSTRACT

The present invention refers to new species of an ion exchange adsorber which is suitable for the separation of host cell proteins (HCPs), antibody fragments and low molecular weight substances from solutions containing antibodies. The invention especially refers to a process for purifying biological samples by separating biomolecules of interest and impurities, comprising steps of contacting a sample with said chromatography media consisting of fibers, said fibers having imparted thereon functionality enabling ion exchange chromatography and/or hydrophobic interaction.

5 Claims, 4 Drawing Sheets

(56) References Cited

U.S. PATENT DOCUMENTS

| | | |
|---|---|---|
| 4,384,957 A | 5/1983 | Crowder et al. |
| 4,512,897 A | 4/1985 | Crowder et al. |
| 4,657,742 A | 4/1987 | Beaver |
| 4,675,104 A | 6/1987 | Rai et al. |
| 4,721,572 A | 1/1988 | Jordan |
| 5,162,074 A | 11/1992 | Hills |
| 5,360,540 A | 11/1994 | Andelman |
| 5,468,847 A | 11/1995 | Heilmann et al. |
| 5,502,022 A | 3/1996 | Schwarz et al. |
| 5,800,706 A | 9/1998 | Fischer |
| 5,886,154 A | 3/1999 | Lebing et al. |
| 5,906,747 A | 5/1999 | Coffman et al. |
| 5,948,528 A | 9/1999 | Helms et al. |
| 6,001,889 A | 12/1999 | Lefebvre |
| 6,008,036 A | 12/1999 | Fanget et al. |
| 6,099,960 A | 8/2000 | Tennent et al. |
| 6,099,965 A | 8/2000 | Tennent et al. |
| 6,228,995 B1 | 5/2001 | Lee |
| 6,254,883 B1 | 7/2001 | Jarnstrom et al. |
| 6,270,970 B1 | 8/2001 | Smith et al. |
| 6,736,973 B1 | 5/2004 | Podgornik et al. |
| 6,811,874 B2 | 11/2004 | Tanaka et al. |
| 7,026,154 B1 | 4/2006 | Gaillac et al. |
| 7,291,263 B2 | 11/2007 | Ward et al. |
| 7,311,825 B2 | 12/2007 | Shah |
| 7,374,673 B2 | 5/2008 | Marcus |
| 7,385,040 B2 | 6/2008 | Johansson et al. |
| 7,465,397 B2 | 12/2008 | Siwak et al. |
| 7,510,848 B2 | 3/2009 | Hammond et al. |
| 7,517,381 B2 | 4/2009 | Rohrbach et al. |
| 7,714,112 B2 | 5/2010 | Engstrand et al. |
| 8,053,565 B2 | 11/2011 | Snyder |
| 8,129,019 B2 | 3/2012 | Pourdeyhimi et al. |
| 8,137,561 B2 | 3/2012 | Kozlov et al. |
| 8,536,288 B2 | 9/2013 | Furumoto et al. |
| 8,722,757 B2 | 5/2014 | Janke et al. |
| 9,029,517 B2 | 5/2015 | Yavorsky et al. |
| 9,284,663 B2 | 3/2016 | Pourdeyhimi et al. |
| 9,815,050 B2 | 11/2017 | Yavorsky et al. |
| 10,449,517 B2 | 10/2019 | Amara et al. |
| 2002/0037565 A1 | 3/2002 | Blanche et al. |
| 2002/0050470 A1 | 5/2002 | Jinno et al. |
| 2002/0058625 A1 | 5/2002 | Mitterer et al. |
| 2002/0177693 A1 | 11/2002 | Lebing et al. |
| 2003/0127393 A1 | 7/2003 | Tepper et al. |
| 2003/0146156 A1 | 8/2003 | Siwak et al. |
| 2003/0180936 A1 | 9/2003 | Memarzadeh et al. |
| 2005/0023221 A1 | 2/2005 | Marcus |
| 2005/0072737 A1 | 4/2005 | Ward et al. |
| 2005/0080251 A1 | 4/2005 | Lemmens |
| 2005/0260911 A1 | 11/2005 | Ochi et al. |
| 2006/0003073 A1 | 1/2006 | Etzel et al. |
| 2006/0032816 A1 | 2/2006 | Marcus et al. |
| 2006/0070950 A1 | 4/2006 | Rasmussen et al. |
| 2006/0073527 A1 | 4/2006 | Albitar et al. |
| 2006/0275781 A1 | 12/2006 | Pham et al. |
| 2007/0102363 A1 | 5/2007 | Little et al. |
| 2007/0292442 A1 | 12/2007 | Wan et al. |
| 2008/0105612 A1 | 5/2008 | Chappas |
| 2008/0108265 A1 | 5/2008 | Pourdeyhimi et al. |
| 2008/0203029 A1 | 8/2008 | Deorkar et al. |
| 2009/0130738 A1 | 5/2009 | Kozlov |
| 2009/0176052 A1 | 7/2009 | Childs et al. |
| 2010/0047904 A1 | 2/2010 | Forde et al. |
| 2010/0058542 A1 | 3/2010 | Kourda et al. |
| 2010/0136025 A1 | 6/2010 | Hickman et al. |
| 2010/0176051 A1 | 7/2010 | Shimagaki |
| 2010/0311850 A1 | 12/2010 | Wickert et al. |
| 2010/0330119 A1 | 12/2010 | Yamamoto et al. |
| 2011/0033633 A1 | 2/2011 | Bothof et al. |
| 2011/0065901 A1 | 3/2011 | Soice et al. |
| 2011/0076771 A1 | 3/2011 | Gabriele et al. |
| 2011/0142863 A1 | 6/2011 | Iyer et al. |
| 2011/0165645 A1 | 7/2011 | Xiong |
| 2011/0206687 A1 | 8/2011 | Hickman |
| 2012/0021796 A1 | 1/2012 | Coulombe |
| 2012/0029176 A1 | 2/2012 | Yavorsky et al. |
| 2012/0074611 A1 | 3/2012 | Zhou et al. |
| 2012/0074612 A1 | 3/2012 | Scrivens et al. |
| 2012/0077249 A1 | 3/2012 | Ramaswamy et al. |
| 2012/0077404 A1 | 3/2012 | Scrivens et al. |
| 2012/0077405 A1 | 3/2012 | Zhou et al. |
| 2012/0077406 A1 | 3/2012 | Scrivens et al. |
| 2012/0148841 A1 | 6/2012 | Pourdeyhimi et al. |
| 2012/0193278 A1 | 8/2012 | Kozlov et al. |
| 2012/0264920 A1 | 10/2012 | Wang et al. |
| 2013/0109769 A1 | 5/2013 | Tsuzuki |
| 2013/0112625 A1 | 5/2013 | Bahukudumbi et al. |
| 2013/0115837 A1 | 5/2013 | Kitchen et al. |
| 2013/0211054 A1 | 8/2013 | Choi et al. |
| 2013/0245139 A1 | 9/2013 | Kozlov et al. |
| 2014/0193876 A1 | 7/2014 | Goerke et al. |
| 2014/0296464 A1 | 10/2014 | Bracewell et al. |
| 2014/0301977 A1 | 10/2014 | Nadarajah et al. |
| 2015/0258540 A1 | 9/2015 | Yavorsky et al. |
| 2015/0352465 A1 | 12/2015 | Amara et al. |
| 2017/0165638 A1 | 6/2017 | Amara et al. |
| 2017/0298091 A1 | 10/2017 | Stone et al. |
| 2018/0085743 A1 | 3/2018 | Yavorsky et al. |

FOREIGN PATENT DOCUMENTS

| | | |
|---|---|---|
| CN | 101036876 A | 9/2007 |
| CN | 101146609 A | 3/2008 |
| CN | 101454025 A | 6/2009 |
| CN | 101617072 A | 12/2009 |
| CN | 101768206 A | 7/2010 |
| CN | 102574911 A | 7/2012 |
| CN | 102711828 A | 10/2012 |
| CN | 102911250 A | 2/2013 |
| CN | 103084222 A | 5/2013 |
| CN | 103153423 A | 6/2013 |
| CN | 103228672 A | 7/2013 |
| CN | 103379949 A | 10/2013 |
| CN | 103732610 A | 4/2014 |
| CN | 104023804 A | 9/2014 |
| CN | 104042714 A | 9/2014 |
| EP | 0269462 A2 | 6/1988 |
| EP | 1141249 A1 | 10/2001 |
| EP | 1796807 A2 | 6/2007 |
| EP | 2036584 A1 | 3/2009 |
| EP | 2087153 A2 | 8/2009 |
| EP | 2089563 A2 | 8/2009 |
| EP | 2266675 A2 | 12/2010 |
| EP | 2336304 A1 | 6/2011 |
| EP | 2346897 A2 | 7/2011 |
| EP | 2266675 A3 | 9/2011 |
| EP | 2727930 A1 | 5/2014 |
| EP | 2883882 A1 | 6/2015 |
| JP | 62-4440 A | 1/1987 |
| JP | 1-297149 A | 11/1989 |
| JP | 5-239709 A | 9/1993 |
| JP | 8-108069 A | 4/1996 |
| JP | 8-170958 A | 7/1996 |
| JP | 11-279945 A | 10/1999 |
| JP | 2000-504002 A | 4/2000 |
| JP | 2000-510201 A | 8/2000 |
| JP | 2003-524157 A | 8/2003 |
| JP | 2008-510142 A | 4/2008 |
| JP | 2010-509099 A | 3/2010 |
| JP | 2011-128147 A | 6/2011 |
| JP | 2013-535683 A | 9/2013 |
| JP | 2013-539787 A | 10/2013 |
| JP | 2014-512340 A | 5/2014 |
| KR | 10-0522108 B1 | 2/2000 |
| KR | 10-2009-0102745 A | 9/2009 |
| KR | 10-2013-0031351 A | 3/2013 |
| WO | 93/10899 A2 | 6/1993 |
| WO | 97/27844 A1 | 8/1997 |
| WO | 99/34916 A1 | 7/1999 |
| WO | 99/44053 A2 | 9/1999 |
| WO | 00/40702 A1 | 7/2000 |
| WO | 01/092552 A2 | 12/2001 |
| WO | 02/083893 A2 | 10/2002 |

(56) References Cited

FOREIGN PATENT DOCUMENTS

| | | |
|---|---|---|
| WO | 03/027366 A1 | 4/2003 |
| WO | 2005/011849 A2 | 2/2005 |
| WO | 2005/021844 A2 | 3/2005 |
| WO | 2006/020640 A2 | 2/2006 |
| WO | 2008/006780 A1 | 1/2008 |
| WO | 2008/039136 A1 | 4/2008 |
| WO | 2008/057426 A2 | 5/2008 |
| WO | 2008/057431 A2 | 5/2008 |
| WO | 2009/146321 A1 | 12/2009 |
| WO | 2009/151593 A1 | 12/2009 |
| WO | 2010/036774 A1 | 4/2010 |
| WO | 2010/048192 A2 | 4/2010 |
| WO | 2010/072381 A1 | 7/2010 |
| WO | 2010/096704 A2 | 8/2010 |
| WO | 2012/015908 A2 | 2/2012 |
| WO | 2012/044382 A1 | 4/2012 |
| WO | 2012/051147 A1 | 4/2012 |
| WO | 2012/068442 A1 | 5/2012 |
| WO | 2012/141791 A1 | 10/2012 |
| WO | 2013/002330 A1 | 1/2013 |
| WO | 2013/068603 A2 | 5/2013 |
| WO | 2014/024514 A1 | 2/2014 |
| WO | 2014/120387 A1 | 8/2014 |
| WO | 2014/126575 A1 | 8/2014 |
| WO | 2014/129964 A2 | 8/2014 |
| WO | 2014/179665 A1 | 11/2014 |
| WO | 2016/093926 A1 | 6/2016 |

OTHER PUBLICATIONS

International Preliminary Report on Patentability dated Feb. 14, 2013 in co-pending PCT application No. PCT/JS2011/045519.
International Search Report and Written Opinion dated Apr. 8, 2014 in co-pending PCT application No. PCT/JS14/10158.
International Search Report and Written Opinion dated Nov. 5, 2015 in co-pending PCT application No. PCT/JS15/45873.
International Preliminary Report on Patentability dated Mar. 16, 2017 in co-pending PCT application No. PCT/JS2015/045873.
International Search Report and Written Opinion dated Apr. 12, 2015 in corresponding PCT application No. PCT/JS2015/053140.
International Preliminary Report on Patentability dated Jun. 22, 2017 in corresponding PCT application No. PCT/US2015/053140.
Canadian communication dated Nov. 29, 2018 in corresponding Canadian patent application No. 2,966,515.
Chinese communication, with English translation, dated Apr. 14, 2014 in co-pending Chinese patent application No. CN 201180037517.2.
Chinese communication, with English translation, dated Jun. 2, 2016 in co-pending Chinese patent application No. 201480006972.X.
Chinese communication, with English translation, dated Dec. 5, 2016 in co-pending Chinese patent application No. 201180037517.2.
Chinese communication, with English translation, dated Jun. 23, 2017 in co-pending Chinese patent application No. 201380021431.X.
Chinese communication, with English translation, dated Jul. 27, 2018 in co-pending Chinese patent application No. 201580047255.6.
European communication dated Jun. 19, 2017 in co-pending European patent application No. 11813102.8.
European communication dated Apr. 12, 2018 in co-pending European patent application No. 15838269.7.
Japanese Communication, with English translation, dated Jan. 7, 2014 in co-pending Japanese patent application No. JP 2013-523201.
Japanese communication, with English translation, dated Jan. 6, 2015 in co-pending Japanese patent application No. 2013-523201.
Japanese communication, with English translation, dated May 10, 2016 in co-pending Japanese patent application No. 2015-135562.
Japanese communication, with English translation, dated Aug. 30, 2016 in co-pending Japanese patent application No. 2015-556020.
Japanese communication, with English translation, dated Mar. 27, 2018 in co-pending Japanese patent application No. 2017-511980.
Japanese communication, with English translation, dated Jul. 17, 2018 in corresponding Japanese patent application No. 2017-530167.
Japanese communication, with English translation, dated May 14, 2019 in corresponding Japanese patent application No. 2017-530167.
Korean communication, with English translation, dated Dec. 1, 2014 in co-pending Korean patent application No. 10-2014-7025710.
Korean communication, with English translation, dated Jan. 29, 2016 in co-pending Korean patent application No. 10-2015-7002666.
Korean communication, with English translation, dated Dec. 1, 2017 in co-pending Korean patent application No. 10-2017-7000772.
Korean communication, with English translation, dated Jul. 30, 2018 in co-pending Korean patent application No. 10-2017-7000772.
Amara et al., "New Disposable Technology for the Chromatographic Purification of Biopharmaceuticals", 245th ACS National Meeting and Exposition, Apr. 7, 2013, Divisions, Pub #45.
Aranha-Creado et al., "Application of Bacteriophages as Surrogates for Mammalian Viruses: A Case for Use in Filter Validation Based on Precedent and Current Practices in Medical and Environmental Virology", PDA Journal of Pharmaceutical Science and Technology, Mar.-Apr. 1999, vol. 53, No. 2, pp. 75-82.
Asher et al., "Technical Report No. 47 Preparation of Virus Spikes Used for Virus Clearance Studies", Parenteral Drug Association, 2010.
Berns et al., Chapter 65, "Parvoviridae," in Fields, Fields Virology, 2007.
Bolton et al., "Normal-flow virus filtration: detection and assessment of the endpoint in bioprocessing", Biotechnology and Applied Biochemistry, vol. 42, Issue 2, Oct. 2005, Abstract.
Brorson, "Phages used as alternatives for mammalian viruses", Powerpoint Presentation.
Brorson et al., "Characterization and purification of bacteriophages using chromatofocusing", Journal of Chromatography A, vol. 1207, Issues 1-2, Oct. 2008, pp. 110-121.
Brunazzi et al., "An Economical Criterion for Packed Absorption Column Design," Chemical and Biochemical Engineering Quarterly, 15 (4), pp. 199-206, 2002.
Bruss et al., "Topological Defects, Surface Geometry and Cohesive Energy of Twisted Filament Bundles," Soft Matter, vol. 9, Issue 34, pp. 8327-8345, 2013.
Chahal et al., "Primary Recovery and Chromatographic Purification of Adeno-associated Virus Type 2 Produced by Baculovirus/Insect Cell System," Journal of Virological Methods, vol. 139, pp. 61-70, 2007.
Chauhan, Principles of Biochemistry and Biophysics, 1st Edition, University Science Press, New Delhi, 2008, p. 31, Introduction to the Concepts of Chemistry.
Choi et al., "Characterization of non-uniformly charged ion-exchange membranes prepared by plasma-induced graft polymerization", Journal of Membrane Science, vol. 268, Issue 2, Jan. 2006, pp. 165-174.
Clayden, et al.. Organic Chemistry, 1st Edition, Oxford University Press: Oxford, 2001, pp. 203-204, Neutral oxygen bases.
Hamaker et al., "Transport Properties of Rolled, Continuous Stationary Phase Columns," Biotechnology Progress, vol. 14, pp. 21-30, 1998.
Marcus et al., "Capillary-Channeled Polymer Fibers as Stationary Phases in Liquid Chromatography Separations," Journal of Chromatography A, vol. 986, pp. 17-31, 2003.
Miesegaes et al., "Viral Clearance by Flow-Through Mode Ion Exchange Columns and Membrane Adsorbers", Biotechnology Progress, vol. 30, Issue 1, 2014, pp. 124-131.

(56) References Cited

OTHER PUBLICATIONS

Müller et al., "Geosynthetics in geoenvironmental engineering", Science and Technology of Advanced Materials, vol. 16, No. 3, May 2015.
Kawai et al., "Protein Binding to Polymer Brush, Based on Ion-Exchange, Hydrophobic, and Affinity Interactions", Journal of Chromatography B, vol. 790, pp. 131-142, 2003.
Koo, et al., AAPS PharmSciTech, vol. 12, No. 2, Jun. 2011, pp. 746-754, "Investigation into Stability of Poly(Vinyl Alcohol)-Based Opadry II Films".
Rowland et al., "Pore Structure Analysis of Purified, Sodium Hydroxide-Treated and Liquid Ammonia-Treated Dotton Celluloses," Journal of Applied Polymer Science, vol. 29, pp. 3349-3357, 1984.
Schure et al., "Simulation of Ordered Packed Beds in Chromatography," Journal of Chromatography A, vol. 1031, pp. 79-85, 2004.
Stanelle et al., "Hydrodynamic flow in capillary-channel fiber columns for liquid chromatography", Journal of Chromatography A, vol. 1100, 2005, pp. 68-75.
Wang, et al., Biotechnol. Prog. 2003, vol. 19, No. 2, pp. 464-468, "Recovery of Acinetobacter radioresistens Lipase by Hydrophobic Adsorption to n-Hexadecane Coated on Nonwoven Fabric".
Zhu Ping, "Functional Fibers and Functional Textiles," China Textile & Apparel Press, 1st Edition, p. 218, Aug. 2006.
U.S. Appl. No. 61/415,605, "High-Surface Area Fibers and Nonwoven Membranes for Use in Bioseparations", 35 pages, filed Nov. 19, 2010 by Gurgel, et al.
"Technical Report No. 41 Virus Filtration", PDA Journal of Pharmaceutical Science and Technology, vol. 59, 2005.
Evans et al., Evans pKa Table, 2005.
GE Healthcare, "Strategies for Protein Purification, Handbook", 2010.
Office action dated Jun. 8, 2018 in co-pending U.S. Appl. No. 15/677,526.
Final rejection dated Dec. 17, 2018 in co-pending U.S. Appl. No. 15/677,526.
Office action dated Apr. 17, 2019 in co-pending U.S. Appl. No. 15/677,526.
Final rejection dated Nov. 8, 2019 in co-pending U.S. Appl. No. 15/677,526.
Office action dated Nov. 15, 2016 in co-pending U.S. Appl. No. 14/759,426.
Final rejection dated Mar. 27, 2017 in co-pending U.S. Appl. No. 14/759,426.
Office action dated Sep. 19, 2017 in co-pending U.S. Appl. No. 14/759,426.
Office action dated Mar. 13, 2019 in co-pending U.S. Appl. No. 15/521,428.
Office action dated Jun. 13, 2019 in co-pending U.S. Appl. No. 15/521,428.
Korean communication, with English translation, dated Jan. 13, 2020 in corresponding Korean patent application No. 10-2017-7014046.
Kallberg et al., "Multimodal Chromatography: An Efficient Tool in Downstream Processing of Proteins", Biotechnology Journal, vol. 7, pp. 1485-1495, Dec. 2012.
Chinese communication, with English translation, dated Jun. 3, 2020 in corresponding Chinese patent application No. 201580066865.0.
Hou et al., "Weak Anion and Cation Exchange Mixed-bed Microcolumn for Protein Separation", Journal of Separation Science, vol. 33, pp. 3299-3303, Nov. 2010.
Chinese communication, with English translation, dated Apr. 9, 2021 in corresponding Chinese patent application No. 201580066865.0.
El Rassi et al., "Tandem Columns and Mixed-bed Columns in High-Performance Liquid Chromatography of Proteins"; Journal of Chromatography, vol. 359, pp. 255-264, 1986.
Boschetti et al., "Mixed-bed Chromatography as a way to Resolve Peculiar Fractionation Situations", Journal of Chomatography B, vol. 897, pp. 827-835, 2011.
Megelski et al., "Micro- and Nanostructured Surface Morphology on Electrospun Polymer Fibers", Macromolecules, vol. 35, pp. 8456-8466, 2002.
Mino et al., "A New Method for the Preparation of Graft Copolymers. Polymerization Initiated by Ceric Ion Redox Systems", Journal of Polymer Science, vol. 31, pp. 242-243, 1958.
Mino et al., "The Polymerization of Acrylamide Initiated by Ceric Nitrate-3-Chloro-1-Propanol Redox Systems", Journal of Polymer Science, vol. 38, pp. 393-401, 1959.
Office action dated Oct. 28, 2021 in co-pending U.S. Appl. No. 15/677,526.

MIXED BED ION EXCHANGE ADSORBER

This application is a divisional of U.S. patent application Ser. No. 15/521,428 filed on Apr. 24, 2017 (the disclosure of which is hereby incorporated by reference), which is a 371 of International Application No. PCT/US2015/053140 filed Sep. 30, 2015, which claims priority of U.S. Patent Application Ser. No. 62/089,030 filed Dec. 8, 2014.

The present invention refers to new species of an ion exchange adsorber which is suitable for the separation of host cell proteins (HCPs), antibody fragments and low molecular weight substances from solutions containing antibodies. The invention especially refers to a process for purifying biological samples by separating biomolecules of interest and impurities, comprising steps of contacting a sample with said chromatography media consisting of fibers, said fibers having imparted thereon functionality enabling ion exchange chromatography and/or hydrophobic interaction.

BACKGROUND

Purification of Monoclonal Antibodies

Since monoclonal antibodies (mAbs) are used for pharmaceutical applications, they are required in exceptionally high purities [A. Jungbauer, G. Carta, in: Protein Chromatography, Process Development and Scale-Up; WILEY-VCH Verlag, Weinheim (Germany) 2010].

In general mammalian cell cultures are employed to manufacture the majority of therapeutic monoclonal antibodies mAb) currently on the market. Production of these drug antibodies typically starts in a bioreactor that contains a suspension of Chinese Hamster Ovary (CHO) cells which secrete the antibody into the extracellular fluid. The resulting antibodies are then subjected to a series of processes including clarification, filtration, and purification that removes cells, cell debris, host cell proteins (HCP), lipids, DNA, viruses, bacteria, antibody aggregates, etc. This series of processes is often referred to as a downstream process (DSP).

Figure 1:
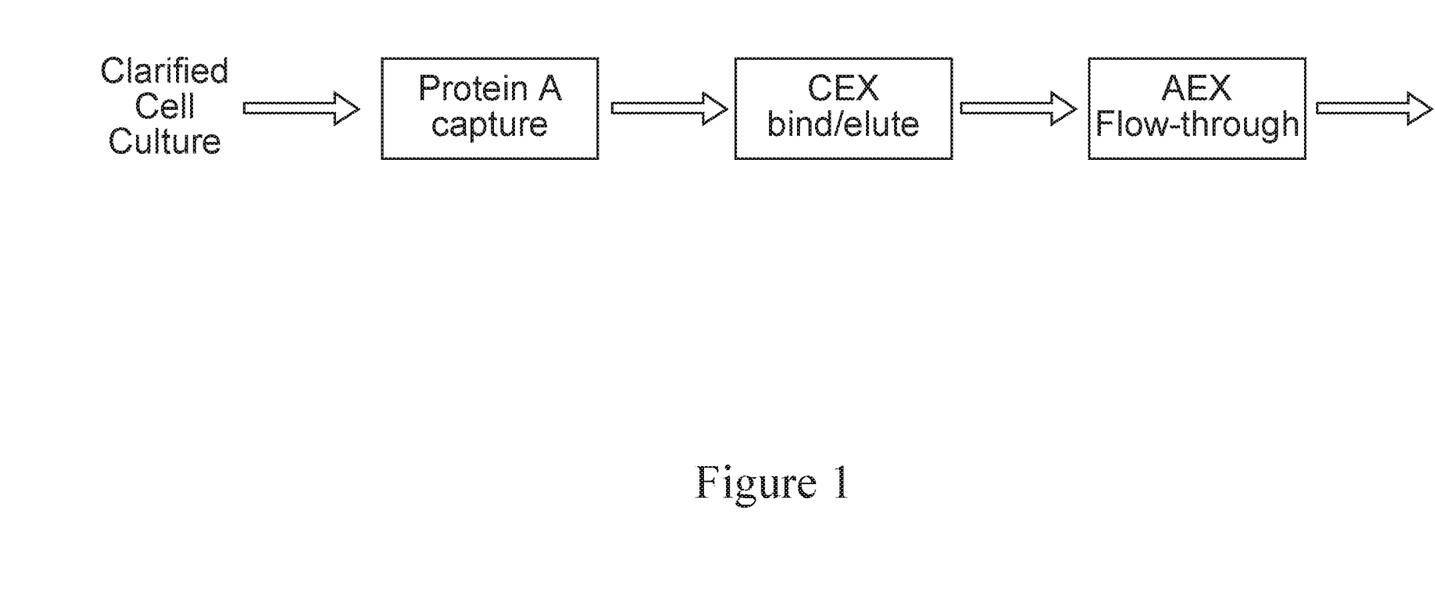
FIG. 1: A standard mAb purification scheme is shown, which employs DSP including a bind-elute chromatography purification step followed by a flow-through polishing step.

Most commonly employed DSP includes one or two bind-elute chromatography purification steps followed by one or two flow-through polishing steps (FIG. 1, standard mAb purification scheme). Typical downstream purification processes employ packed columns filled with porous bead-based chromatography media or membrane-based devices. These unit operations are employed in series and each are targeted towards clearing a particular impurity in either a flow-through polishing or a bind/elute capture mode.

One of the primary objectives of the polishing media is to reduce the concentration of HCP down to <10 ppm (in reference to mAb concentration). The commercial scale purification of various therapeutic biomolecules is currently accomplished using bead-based chromatography resins. Biopharmaceutical manufacturers most commonly use simple anion-exchange (AEX) chromatography media in this flow-through polishing step. The AEX media is employed to remove acidic HCP, DNA, endotoxins, and viruses. However, it is often less effective in removing positively charged impurities, such as basic HCP, product aggregates and fragments.

Monoclonal antibodies continue to gain importance as therapeutic and diagnostic agents. The process of screening hybridoma libraries for candidate mABs is both time consuming and labor intensive. Once a hybridoma cell line expressing a suitable mAB is established, a purification methodology must be developed to produce sufficient mAB for further characterization.

A traditional method for purifying involves using Protein A or Protein G affinity chromatography, as well as ion exchange chromatography. The purified antibody is desalted and exchanged into a biological buffer using dialysis. The entire process typically requires several days to complete and can be particularly onerous if multiple mABs are to be evaluated in parallel.

Thus, a variety of new polishing adsorbers have been developed recently, which show greater capacities and affinities allowing them to remove a broader range of impurities. These adsorbers include so-called "mixed-mode" ligands, both anion (AEX) (e.g. U.S. Pat. No. 7,714,112) and cation exchange (CEX) materials (e.g. U.S. Pat. No. 7,385,040). However, the higher cost of these sophisticated ligands on resins precludes their employment for single use or in disposable processes.

In general the applied bead-based adsorbers demonstrate a high porosity and large surface areas that provide materials with sufficient adsorptive capacities for the batch processing of biomolecules at production scales (e.g., 10,000 liters). From patent literature numerous examples are known of such bead-based media used in mixed bed stationary phases for this technical application.

In JP 01-10178 (Asahi Chem. Ind. CO LTD., also published as JP 2660261B2) a multifunctional module is disclosed which comprises a combination of AEX and CEX porous hollow fiber membranes for the purpose of removing cations, anions and fine particles within a single device.

Bio-Rad Laboratories, Inc. has developed a multi-media affinity column (U.S. Pat. No. 8,053,565 B) comprising a layering of an affinity chromatography media above a second type of chromatography media in a single column so that the second lower chromatography media will capture any leached affinity ligands from the upper affinity chromatography media during the process of eluting the affinity bound protein of interest.

Promega Corp. (U.S. Pat. No. 6,270,970 A) has developed a mixed bed solid phase for the isolation of nucleic acids from an impure mixture. Each of the comprising two phases has the capacity to bind and release the target nucleic acid under different solution conditions.

In a further patent application (WO 2005/011849 A), filed by Millipore Corp. and Ebara Corp., an electro-deionization module is disclosed, wherein the ion-exchange means is comprised of an assembly of a fabric of anion exchange fibers and a fabric of cation exchange fibers which are placed in a face to face relationship.

Mixed-bed chromatography employs two or more different adsorbent media that are combined together in a single device. It allows a variety of different interactions applied to be used for analysis and purification of protein solutions within a single device. Rassi and Horváth demonstrated that a mixed-bed column composed of AEX-resin and CEX resin gave similar separation of proteins as two separate columns linked in series (el Rassi, Z.; Harváth, C.; "Tandem columns and mixed-bed columns in high-performance liquid chromatography of proteins"; J. Chrom. 1986, 359, 255-264). Using these systems, they were able to resolve a mixture of several different proteins that would elute simultaneously when only a single resin was employed.

Mixed-bed chromatography has been applied to several different applications including the analysis of proteomes, which are particularly difficult to analyze since they are composed of a variety of both high-abundance and lowabundance proteins (Boschetti, E.; Righetti, P. G.; "Mixed-bed chromatography as a way to resolve peculiar fractionation situations", J. Chomatogr. B 2011, 897, 827-835.

Separation materials, like chromatography resins typically present a spherical structure that enables an efficient column packing with minimal flow non-uniformities. The interstitial spaces between the beads provide flow channels for convective transport through the chromatography column. This enables chromatography columns to be run with large bed depths at a high linear velocity with a minimal pressure drop. The combination of these factors enables chromatography resins to present the required efficiency, high permeability, and sufficient binding capacity that are required for the large-scale purification of biomolecules.

In bead-based chromatography, most of the available surface area for adsorption is internal to the bead. Consequently, the separation process is inherently slow since the rate of mass transport is typically controlled by pore diffusion. To minimize this diffusional resistance and concomitantly maximize dynamic binding capacity, small diameter beads can be employed. However, the use of small diameter beads comes at the price of increased column pressure drop. Consequently, the optimization of preparative chromatographic separations often involves a compromise between efficiency/dynamic capacity (small beads favored) and column pressure drop (large beads favored).

Chromatography media typically has a very high cost (>$1000/L) and significant quantities are required for large scale production columns. As a result, biopharmaceutical manufacturers recycle chromatography resins hundreds of times. Each of these regeneration cycles consumes substantial quantities of media, and each step incurs additional costs associated with the validation of each cleaning, sterilization, and column packing operation.

As indicated above, several technologies are described in the patent literature and marketed commercially for biopharmaceutical separations based on functionalized fibrous media and/or composites. Most rely on incorporating a porous gel into the fiber matrix, the gel providing the needed surface area to gain reasonable binding capacities. However, in such constructions, poor uniformity in gel location and mass generally leads to poor efficiencies (shallow breakthrough and elution fronts). In addition, resistance to flow can be high, even for short bed depths, a problem often aggravated by gel compression under modest pressure loads.

Another approach taken has been the incorporation of particulates within the fiber matrix, the particulates often are porous and possessing a native adsorptive functionality; examples being activated carbon and silica gel.

Object

The current downstream process (DSP) is complex and expensive. This is why the industry is interested in the development of new technologies to compress, simplify, and reduce the costs of these processes. Therefore, it is an objective to develop inexpensive disposable adsorbent media that reduces manufacturing costs by eliminating the time and buffers required to clean and to store the column after use. It is also an objective to increase the performance of the adsorbent media by targeting a wider variety of impurities.

In addition, it is desirable to have a customizable composition of ligand chemistries so that the adsorbent media can be specifically tuned to target the particular mixture of impurities present in a given feed. This is challenging to accomplish with resin- and membrane-based adsorbent media.

It is also desirable to provide a combination of a high surface area fiber with pendant adsorptive functionality for biomolecule chromatography applications, without sacrificing bed permeability and attainable flow rates.

In addition to this, it is also an object of the present invention to provide an inexpensive, manufacturable and chemically defined carrier material that can be derivatized by conventional procedures so that it can be used both as ion exchanger material or as a hydrophobic separator material.

SUMMARY OF THE INVENTION

The shortcomings of the prior art have been addressed by the embodiments disclosed herein, which relate to an adsorptive media for chromatography, particularly ion exchange chromatography and especially a corresponding process for purifying biological samples using this media.

The process for purifying a biological sample disclosed here by separating a biomolecule of interest and impurities comprises the steps of contacting the sample with a chromatography media consisting of fibers, said fibers having imparted thereon functionality enabling ion exchange chromatography and/or hydrophobic interaction and comprises steps of washing either to remove unbound species or to extract said biomolecule of interest.

In detail, a process for purifying a sample comprising a biomolecule of interest and impurities according to the present invention in general comprises the steps of a) providing a sample,
b) contacting said sample with a first chromatography media comprising fibers, said fibers having imparted thereon functionality enabling ion-exchange chromatography or hydrophobic interaction chromatography,
c) washing said first fiber media to remove unbound species,
d) washing said first fiber media to extract said biomolecule of interest,
e) contacting said biomolecule of interest with a second chromatography media comprising fibers, said fibers having imparted thereon functionality enabling ion-exchange chromatography or hydrophobic interaction chromatography,
f) washing said second fiber media to remove unbound species, and
g) washing said second fiber media to extract said biomolecule of interest, but with the proviso that differently functionalized fiber media are used in steps b) and e).

In step b) the applied sample is contacted with a first chromatography media comprising fibers, said fibers having imparted functionality enabling anion-exchange chromatography, and wherein in step e) chromatography media are used comprising fibers having functionality enabling hydrophobic interaction chromatography. However this process can also be carried out in a modified form, wherein in step b) said sample is contacted with a first chromatography media comprising fibers, said fibers having imparted functionality enabling cation-exchange chromatography, and wherein in step e) chromatography media are used comprising fibers having functionality enabling hydrophobic interaction chromatography. In another embodiment of this process in step b) chromatography media are used comprising fibers having functionality enabling hydrophobic interaction chromatography, and in step e) said ion-exchange chromatography is anion-exchange chromatography or cation-exchange chromatography. But it is also possible, depending on the nature of applied biological sample that in step b)

chromatography media are used comprising fibers having functionality enabling anion-exchange chromatography and that said second chromatography media in step e) is cation-exchange chromatography or vice versa.

In another embodiment of the inventive process steps are as follows:
a) providing a sample,
b) contacting said sample with a mixture of a first chromatography media comprising fibers and a second chromatography media comprising fibers, said first chromatography media comprising fibers having imparted thereon functionality enabling ion exchange chromatography, said second chromatography media comprising fibers having imparted thereon functionality enabling ion exchange chromatography,
c) washing said mixture of chromatography media to remove unbound species, and
d) washing said mixture of chromatography media to extract said biomolecule of interest.

Here said first chromatography media is anion-exchange chromatography and said second chromatography media is cation-exchange chromatography or vice versa.

Another variant of the process of the invention is
a) providing a sample,
b) contacting said sample with a mixture of a first chromatography media comprising fibers and a second chromatography media comprising fibers, said first chromatography media comprising fibers having imparted thereon functionality enabling hydrophobic interaction chromatography, said second chromatography media comprising fibers having imparted thereon functionality enabling ion exchange chromatography,
c) washing said mixture of chromatography media to remove unbound species, and
d) washing said mixture of chromatography media to extract said biomolecule of interest.

The second chromatography media comprising fibers having imparted thereon functionality enabling ion exchange chromatography may be either cation-exchange chromatography or anion-exchange chromatography.

The present invention also relates to a housing comprising a packed bed of fibers; said packed bed having a first layer and a second layer, said first layer comprising fibers having imparted thereon functionality enabling ion-exchange chromatography, and said second layer comprising fibers having imparted thereon functionality enabling hydrophobic interaction chromatography. Said ion-exchange chromatography may be anion-exchange chromatography or cation-exchange chromatography. In a special embodiment of the housing according to the invention it comprises a packed bed of fibers; said packed bed having a first layer and a second layer, said first layer comprising fibers having imparted thereon functionality enabling hydrophobic interaction chromatography, and said second layer comprising fibers having imparted thereon functionality enabling ion-exchange chromatography. Said ion-exchange chromatography may be anion-exchange chromatography or cation-exchange chromatography. In another embodiment of the invention the housing comprises a packed bed of fibers; said packed bed having a mixture of a first chromatography media and a second chromatography media, said first chromatography media comprising fibers having imparted thereon functionality enabling hydrophobic interaction chromatography, and said second chromatography media comprising fibers having imparted thereon functionality enabling ion-exchange chromatography. The comprising ion-exchange chromatography may be anion-exchange chromatography or cation-exchange chromatography.

The inventive process for purifying a sample comprising a biomolecule of interest and impurities may also be carried out by contacting a sample, with a first chromatography media comprising fibers, said first fibers having imparted thereon functionality enabling ion-exchange chromatography and contacting it with a second chromatography media comprising fibers, said second fibers also having imparted thereon functionality enabling ion-exchange chromatography. Preferably the first chromatography media are cation-exchange fibers and said second chromatography media are anion-exchange fibers. In another preferred embodiment of the process said first chromatography media are anion-exchange fibers and said second chromatography media are cation-exchange fibers. The chromatography media in this process is selected so that said first functionality enables purification in a flow-through mode and said second functionality enables purification in a flow-through mode. In another embodiment of the inventive process it is selected so that said first functionality enables purification in a bind/elute mode and said second functionality enables purification in a bind/elute mode. If it proves to be advantageous for the purification, the process can however also be modified such that said first functionality enables purification in a flow-through mode and said second functionality enables purification in a bind/elute mode.

Furthermore, the inventive process for purifying a sample comprising a biomolecule of interest and impurities may also be carried out by contacting a sample, with a first chromatography media comprising fibers, said first fibers having imparted thereon functionality enabling ion-exchange chromatography and a second chromatography media comprising fibers, said second fibers having imparted thereon functionality enabling hydrophobic interaction chromatography. In this embodiment of the inventive process, preferably the first chromatography media are cation-exchange fibers and said second chromatography media are hydrophobic interaction chromatography fibers. Otherwise, if the biomolecule of interest it requires said first chromatography media are anion-exchange fibers and said second chromatography media are hydrophobic interaction chromatography fibers. Good purification results are achieved if said first functionality but also said second functionality enable purification in a flow-through mode. If necessary and advantageous the chromatography media may be chosen, wherein said first functionality enables purification in a bind/elute mode and said second functionality enables purification in a bind/elute mode. In another embodiment of the inventive process chromatography media may be chosen such that the first functionality enables purification in a flow-through mode and said second functionality enables purification in a bind/elute mode. Furthermore, in a special embodiment of the inventive process said first chromatography media and said second chromatography media is arranged in a mixture of variously functionalized fibers, or said first chromatography media and said second chromatography media are arranged in layers. Corresponding embodiments of layered chromatography media are described in more detail below.

DETAILED DESCRIPTION OF THE INVENTION

The chromatography media disclosed is derived from a shaped or porous fiber having high surface areas. In certain embodiments, the shaped fiber presents a fibrillated or ridged structure. An example of the high surface area fiber in accordance with certain embodiments is "winged" fibers, commercially available from Allasso Industries, Inc. (Raleigh, N.C.). Suitable fibers, which may be winged or highly porous, present a surface area of approximately 1 to 14 square meters per gram.

Also disclosed herein, fibrous materials are derivatized in a method adding surface pendant functional groups that provide cation-exchange or anion-exchange functionalities, for example, to the high surface area fibers. This pendant functionality is useful for the ion-exchange chromatographic purification of biomolecules, such as monoclonal antibodies (mAbs).

Chromatographic exchanger materials disclosed here comprise nonwoven polymer fibers with high surface areas at least in the range of 1-14 $m^2/g$, which in turn comprise functional groups at their surfaces, namely at least anion exchanging groups, cation exchanging groups or groups with hydrophobic interaction functionalities, and wherein the functional groups may be mixed or as such be attached to the surface of the same fiber and whereby fibers differently functionalized may be combined or mixed with each other. Depending on the performed functionalization the material of the invention is an ion exchange material which is either an anion exchanger or a cation exchange adsorber. In another embodiment of the invention the functionalized chromatographic exchanger material may comprise hydrophobic interaction functionalities either on the surfaces of the same fibers which are already functionalized by ionic groups or on the surfaces of separate fibers.

This means chromatographic exchanger materials of the present invention may comprise fibers having different functionalities or may comprise a mixture of fibers having different functionalities. In a preferred embodiment the materials of the present invention are blended together to present an evenly distributed mixture of the different functional groups within the chromatographic media. The composition of the chromatographic media can be controlled by altering the relative amounts of the two different types of fiber for a specific application. For instance, a chromatographic media composed of 50% anion exchanger fibers (AEX fibers) and 50% cation exchanger fibers (CEX fibers) could be created for a specific application. In another instance, a chromatographic media composed of the 25% AEX fibers and 75% CEX fibers could be created to address the specific separation needs of a different application.

In an alternative embodiment the materials of the present invention have a layered structure, wherein the different layers can be made of the same fibers or wherein each layer may have a different functionality. Thus, layers may follow each other having different functionalities. These layers may follow each other in a special sequence, optionally for several times or layers with the same functionality are repeated in direct succession for several times to generate a desired layer thickness.

Fibers forming the chromatographic exchanger materials are fibers with high surface areas in the range of 1-14 $m^2/g$, which are based either on lightweight winged fibers having eight to 32 deep channels or on highly porous fibers. The winged fibers may be made by coextrusion forming the core features from eight to 32 deep channels between uniform, straight-edged wings. Highly porous fibers can also be used as chromatographic exchanger materials. In general, fibers having a length ranging from 0.5 mm to 5 cm are used for the inventive chromatographic exchanger materials. Preferably chromatographic exchanger materials according to the invention are composed of fibers having a length ranging from 0.5 mm to 2.5 cm. Especially preferred are chromatographic exchanger materials comprising fibers having a length ranging from 0.5 mm to 2 mm.

It has been found as being advantageous if the chromatographic exchanger materials comprise fibers made of a polymer selected from the group polystyrene, polycarbonate, poly(ethyleneoxide), polyester, polypropylene, methyl, methacrylate, (hydroxyethylmethacrylate, poly(propyleneglycol)monomethacrylate, (phenyl)methacrylate, ((n-butyl)methacrylate, (n-hexyl)methacrylate, polybutylene terephthalate (PBT), polyethylene terephthalate (PET), and polyamide.

By means of the chromatographic exchanger materials disclosed here new devices can be produced having significantly improved properties in separation and purification processes of biological fluids. Corresponding devices are therefore also subject of the present invention. By experiments it was found, that devices are particularly suitable comprising chromatographic exchanger materials, wherein the fibers are made of polyamide, polybutylene terephthalate (PBT), polyethylene terephthalate (PET) or polypropylene (PP), especially fibers, which are dervatized with acrylic monomers. The acrylic monomers may be selected from the group 2-hydroxylethyl methacrylate (HEMA), acrylamide, acrylic acid, acrylonitrile, methyl methacrylate and glycidyl methacrylate (GMA). These acrylic monomers can be used for the derivatization as such or in a combination thereof. Especially preferred are corresponding devices wherein the fibers are dervatized with glycidyl methacrylate (GMA) or with a combination of 2-hydroxylethyl methacrylate (HEMA) and glycidyl methacrylate (GMA). According to the present invention these devices are preferably made with such derivatized fibers which in turn are modified by reaction with a compound comprising a functional group or with ligands. Said functional groups are selected from amino, carboxyl, hydroxyl, epoxy, sulfopropyl, sulfonic acid, and sulfhydryl groups.

Since the new devices may be produced using quite inexpensive fibers and processes, they can be made as disposable devices.

The object of the invention is also a method for separating a target agent from a biological sample, which comprises the steps of
  a) providing the sample containing the target agent;
  b) contacting the sample with the chromatographic exchanger material which is disclosed here; and
  c) allowing the target agent to bind to the high-surface area fibers and thereby be separated from the sample.

In a following step (d) the sample resulting from step (c) may be collected, or the sample resulting from step (c) is retrieved in step (d) and in the next step (e) the target agent bound to the nonwoven fibrous material is collected by eluting through the nonwoven material an elution solution interfering with the binding between the target agent and the fibers so as detach the target agent from the fibers. In a special embodiment of this method the nonwoven material is condensed into a sheet or filled and compressed into a column.

This method is especially suitable for separation processes wherein target agents are proteins, peptides, lipids, DNA molecule, RNA molecule, an organic molecule, an inorganic molecule, cells, viruses, bacteria, toxins or a prion.

The chromatography media as described above may be derived from a shaped fiber. It has been found, that in certain embodiments, the shaped fiber presents a fibrillated or ridged structure. These ridges can greatly increase the surface area of the fibers when compared to ordinary fibers. Thus, high surface area is obtained without reducing fiber diameter, which typically results in a significant decrease in bed permeability and a corresponding reduction in flow rate.

An example of the high surface area fiber in accordance with certain embodiments are "winged" fibers, commercially available from Allasso Industries, Inc. (Raleigh, N.C.; Allasso Winged Fiber™). These fibers are made of Nylon and very lightweight and have the same total surface area in the range of 1 to 14 square meters per gram. These fibers comprise a shaped core polymer and a sacrificial polymer that are coextruded through a specially designed spinpack. The core features from eight to 32 deep channels between uniform, straight-edged wings. The sheath polymer fills the channels during fiber formation and is dissolved during finishing of the final product.

As already mentioned earlier highly porous fibers are also applicable in the present invention.

Now, it has been found, that chromatographic purification of biomolecules, such as monoclonal antibodies (mAbs) can be processed under simplified conditions but with improved results when a mixed functionality of this fiber material is utilized, which includes both ionic and hydrophobic interactions.

Thus, a method is developed wherein surface pendent functional groups are added that provide CEX, AEX, or hydrophobic interaction functionalities, for example, to the high surface area fibers.

For the production of suitable functionalized high surface area fibers not only Allasso Winged Fibers made from nylon are applicable but also other fibers showing high surface areas in the range of at least 1 to 14 square meters per gram may be used. For example highly porous fibers may also be applied. Such fibers are disclosed by S. Megelski et al. in Macromolecules 2002, 35, 8456-8466 and are spun from polystyrene, polycarbonate or poly(ethyleneoxide). But also corresponding fibers of polyester, polypropylene (PP), methyl methacrylate, (hydroxyethylmethacrylate, poly(propyleneglycol)monomethacrylate, (phenyl)methacrylate, ((n-butyl)methacrylate, (n-hexyl)methacrylate), polybutylene terephthalate (PBT), polyethylene terephthalate (PET) or polyamide can be used for this purpose. A preferred group of fibers is made of polyamide, polypropylene, polybutylene terephthalate (PBT) or polyethylene terephthalate (PET).

By using these modified high surface area fibers an alternative mode of purification may be provided, which utilizes fiber based chromatography media with pendent AEX and CEX ligands. In one embodiment of this invention, both the AEX fiber and the CEX fiber media are blended and packed into a single device. This format is advantageous in terms of its operational simplicity and the potential for process template compression by this approach.

In another embodiment, advantageous properties have been found for the design of a fiber media for hydrophobic interaction chromatography. Fiber media of this type are useful for a so-called "tandem chromatography", where only one chromatography column is provided and two different types of fiber chromatography media are arranged in discrete layers within this chromatography column.

This special arrangement is suitable for an application where a monoclonal antibody feed stream is purified by bind/elute purification using a CEX fiber media arranged in a first layer, followed by elution and a subsequent purification by hydrophobic interaction chromatography with the described HIC fiber media arranged in a second layer within the same chromatography column or other suitable devices.

The combination of mixed beds of fiber-based ion-exchangers of the type as described here is found to have different unexpected advantages. Especially, fiber media with varying ion exchange or hydrophobic interaction chromatography ligand functionalities can be easily arranged into layered structures, whereas with bead based systems this format cannot be easily achieved.

Mixed-bed chromatography is a particular powerful method for the purification therapeutic proteins derived from recombinant cells since these sources contain a wide variety of host cell protein (HCP) impurities. These protein impurities are particularly challenging to remove at low concentrations when using only a single type of chromatography media. One approach is to arrange several different adsorbent media in a series of columns. However, this will significantly increase the dead volume and complexity of the downstream process. Combining the different adsorbent media into single device allows the different impurities to be removed in a single step.

Unexpectedly a mixed-bed chromatography device composed of AEX functionalized fiber media and CEX functionalized fiber media is highly efficient for the flow-through removal of residual HCP from an antibody elution. The mixed fiber bed allows both positive and negatively charged HCP to be removed. The relative low cost of functionalized fibers allows them to be used as a single-use, disposable application.

Figure 2:
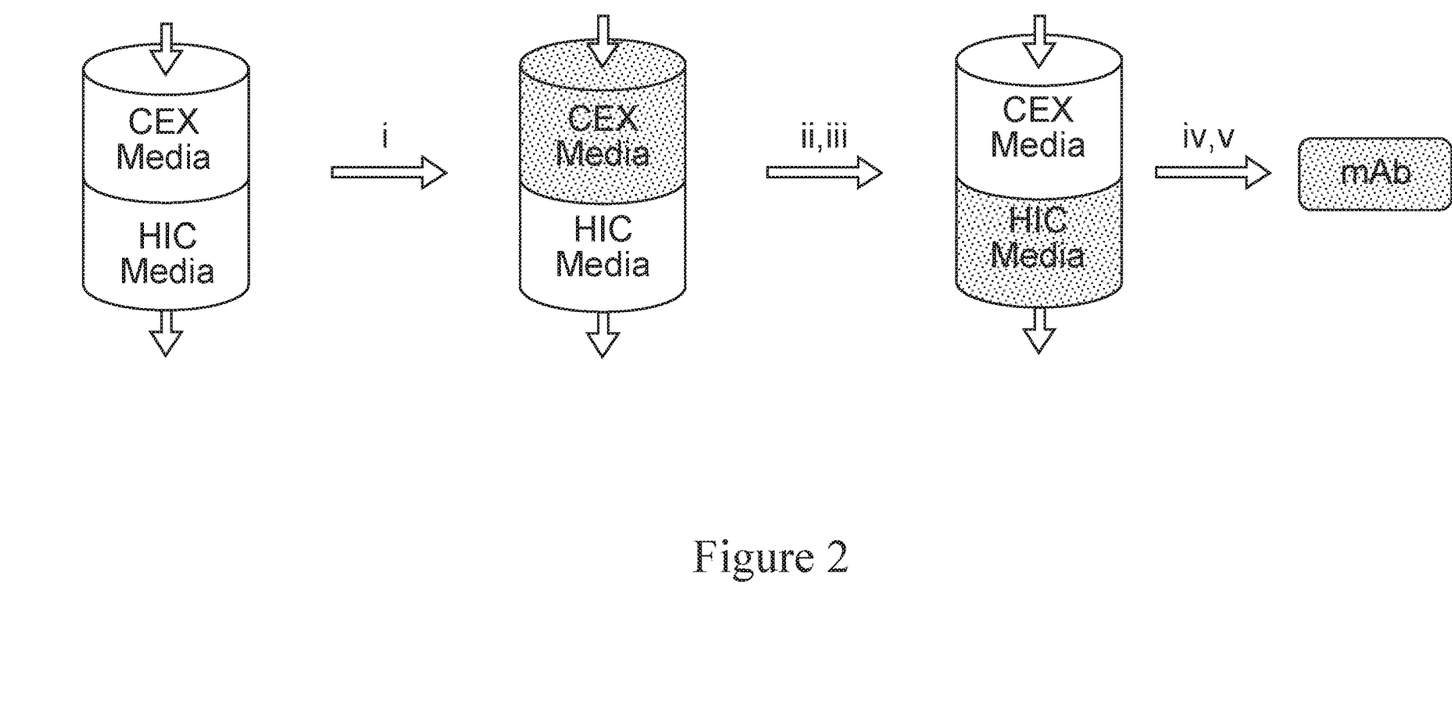
FIG. 2: A schematic flow scheme of the separation process is shown of a mAb purification by tandem chromatography (CEX media and HIC) including the steps:
 i. post-protein A mAb load (conductivity 3 mS, pH 5)
 ii. high salt mAb elution (conductivity 30-100 mS, pH 5), where the product mAb is eluted from the upper CEX media layer but binds to the lower HIC media layer and
 iii. low salt mAb elution (conductivity 3 mS, pH 5), where the product mAb is eluted from the lower HIC media layer by elution with a low ionic strength eluent

According to the present invention the layering of the surface-modified chromatography media into discrete bands within a housing, a single chromatography column or other suitable chromatography device leads to improved separation and purification results. The "layering" is accomplished by first applying a media to the column and compressing the media to a higher density to form the lower layer of media. A second layer can be subsequently applied to the column and the media compressed to a higher density to form the upper layer. Finally, the layered media can be compressed to a third, highest density by installation of the upper flow distribution header on the chromatography column or other suitable chromatography device. It is possible to provide a single column comprising a layered column comprising two types of fiber based chromatography media with different ligands, a CEX ligand (for example as disclosed in Example 3) and a hydrophobic interaction chromatography ligand (for example as disclosed in Example 6), which provides two orthogonal modes of separation. In FIG. 2 a layered media column is disclosed for "tandem chromatography" that provides a first layer of CEX fiber media that is situated on top of a second layer of a HIC fiber media. This format can be utilized for example in the purification of a monoclonal antibody process stream by first applying the post-protein A elution pool (mAb feed) onto the top of the layered column.

In one embodiment, the mAb feed is at a low conductivity (typically 3 mS/cm) and has a pH of 5 after adjustment with appropriate buffer system (FIG. 2). This mAb feed solution is loaded onto the column and first encounters the CEX fiber media layer, where the mAb binds to the fiber media by an ion exchange interaction. The fiber media is washed with an appropriate buffer to clear any unbound HCP, DNA or other impurities. After washing, an elution buffer of a high conductivity (30-1000) mS/cm, pH 5) is applied to the column to elute the mAb from the CEX layer. As the eluted mAb travels into the zone of the column occupied by the HIC fiber media, the mAb binds to the HIC media by a hydrophobic interaction (due to the high ionic strength of the buffer used for elution from CEX media layer). The fiber media is again washed with an appropriate high ionic strength buffer to clear any unbound HCP or other impurities from the HIC fiber media portion of the column. Finally, an elution buffer of a low ionic strength (3 mS/cm, pH 5) is applied to the column to elute the mAb from the HIC layer. The isolated mAb product after this step has a low conductivity and requires only a minor pH adjustment for subsequent AEX-based polishing operations.

FIG. 2 shows the schematic flow of the separation process described above, which is an example of mAb purification by tandem chromatography (CEX media and HIC) including the steps:
i. post-protein A mAb load (conductivity 3 mS, pH 5)
ii. high salt mAb elution (conductivity 30-1000 mS, pH 5), where the product mAb is eluted from the upper CEX media layer but binds to the lower HIC media layer.
iii. low salt mAb elution (conductivity 3 mS, pH 5), where the product mAb is eluted from the lower HIC media layer by elution with a low ionic strength eluent.

[Now, the eluted mAb is ready for a subsequent AEX polishing operation without a need for dilution to reduce the solution conductivity.

As mentioned above, the solution described here provides an inexpensive separation process for mAB, comprising a disposable format and which may be carried out at low material costs. In addition to this, different process steps, which had to be carried out in different columns and filtering devices under repeated reduction of the amount of liquid and adjusting the pH value and the conductivity, are compressed to a procedure carried out in a single column wherein a convective transport of substrate to binding sites takes place.

The surface functionalization of the high surface area fibers can also be accomplished by a two step process. A suitable functionalization process is grafting polymerization as disclosed in WO 2012/015908 A. This functionalization begins with the attachment of pendant allyl groups to the fiber surface, for example to the surface of winged fibers made of Nylon6, a polyamide. Here the fibers are treated with allyl glycidyl ether in the presence of aqueous sodium hydroxide at 50° for 12 hours. This first step of the functionalization of the fiber surface can be carried out as disclosed in the aforementioned patent application or under changed conditions by different suitable monomers, like epichlorohydrin, or (meth)acrylic glycidyl esters. [0058] The pendant allyl groups serve then as anchoring sites on the fiber surface as attachment points for the pendant acrylamide polymer functionality. Conditions for the solution polymerization of acrylamide monomers are provided, and the pendant allyl groups on the fiber surface attach to the growing polymer chains in solution. Thus, the allyl-functionalized fibers may be subsequently treated with an aqueous solution of 2-acrylimido-2-methyl-1-propane sulfonic acid, N,N-dimethylacrylimide and ammonium persulfate at about 80° C. for about 4 hours. Upon heating to this temperature, persulfate decomposition initiates a free radical polymerization of the acrylic monomers. In this reaction a cation exchanger is received, which comprises sulfonic acid groups. Under these conditions, the pendant allyl groups on the fiber surface may serve as attachment points for the pendant acrylic polymer functionality and the acrylic polymer is covalently attached to the fiber surface.

Ceric ion redox grafting polymerizations may also be employed for the surface modification of the high surface area fibers. Under these conditions, the acid may be $HNO_3$ and Ce(VI) ions are provided by a salt like (ammonium cerium(IV) nitrate). In this case the reaction time is much shorter and the temperature lower.

In general the ceric ion redox grafting reaction is processed according to Mino and Kaizerman [Mino, G., Kaizerman, S. J. Polymer Science 31, 242-243 (1958) and J. Polymer Science 38, 393-401 (1959)], which is done in an aqueous nitric acid solution. This reaction can be carried out with monomers, which are soluble in aqueous solutions. If not water-soluble monomers are to be used, the solubility can be improved by suitable solubilizers, such as dioxane or tetrahydrofuran.

In subsequent reaction step, the surface functionalized fibers, for example modified with poly(glycidyl methacrylate), can be converted into an anion exchanger by simply mixing the functionalized fibers with a solution of 50 wt % trimethylamine (aq.) in methanol.

By appropriately adapted grafting reactions and by use of appropriate reactants, it is possible to covalently bind polymer chains, which are not cross-linked and which carry a variety of functional groups, to the surfaces of the applied fibers.

With the term "functional group" are subsumed terms, such as active, hydrolyzable, hydratable, hydrogen bond formation-causing ionogenic (ionizable) charge-carrying (cationic or anionic) group. Examples for such groups are —OH and/or —CO— and/or —$NH_2$ and/or —$SO_3^-$ and/or —$SO_4^-$ and/or —$PO_4^-$ and/or —$SO_2Cl$ and/or —$NH_4^+$ and/or —CONH and/or —CHO and/or —COOH and/or —$COO^-$ and/or —SH.

Thus, suitable functional groups for the anion exchange chromatography are for example quarternary ammonium groups, like quarternary hydroxypropyldiethylaminoethyl-, quarternary trimethylaminoethyl-, or diethylaminoethyl groups. Depending on the degree of ionic dissociation of the functional groups the anion exchangers can be classified as strong, medium or weak base anion exchanger.

In another embodiment of the invention the applied fibers are functionalized as cation exchangers with acidic groups. Suitable functional groups for the cation exchange chromatography are for example sulfomethyl-, sulfopropyl-, or carboxymethyl groups.

Groups suitable for hydrophobic interaction chromatography are for example alkyl and aryl ligands like ether and methyl ligands, which provide weak interactions with proteins, or butyl or octyl ligands, phenyl, or other aryl ligands which show more intense interactions.

Substitution of at least one hydrogen atom with a functional group can indirectly be made via a methylene, ethylene, propylene or butylenes bridge or a corresponding alkoxy or aryl.

As mentioned above, the functional groups can be bound to the surface of the applied fibers by means of suitable graft polymers.

In general, the graft-polymerization is carried out according to known methods in presence of suitable initiators, which may be redox initiators such as ceric (IV) ion (ceric ammonium nitrate: $(NH_4)_2Ce(NO_3)_6$), cerium (IV) sulphate, ceric ammonium sulfate, iron(II)-hydrogen peroxide ($Fe^{2+}$—$H_2O_2$: Fenton reagent), cobalt (III) acetylacetonate complex salts, Co (II)-potassium monopersulfate, sodium sulfite-ammonium persulfate or free radical generators such as azobisisobutyronitrile ($C_8H_{12}N_4$: AIBN), potassium persulfate ($K_2S_2O_8$: KPS), ammonium persulfate (($NH_4)_2S_2O_8$: APS), and benzoyl peroxide ($C_{14}H_{10}O_4$: BPO).

For example, graft-polymerization can be processed using acidic monomers like acrylic acid and methacrylic acid of a suitable ceric (IV) salt. If such monomeric acids are combined, even in a relatively low ratio, with neutral monomers such as methyl methacrylate, methyl acrylate and acrylonitrile grafting on a fiber takes place quite readily. The resulting graft copolymer is a weak acidic, high-capacity, cation exchanger.

Depending on the chemical nature of the fibers employed and the monomers used for derivatization different reactions and mechanisms can occur and possible approaches for appropriate surface modifications are:
- atom transfer radical polymerization (ATRP)
- UV-initiated free radical polymerization
- thermally-initiated free radical polymerization
- anionic polymerization
- cationic polymerization
- gamma-initiated free radical polymerization
- transition metal catalyzed polymerization
- reversible-addition fragmentation transfer polymerization (RAFT)

There are various suitable monomers for carrying out the graft-polymerization. Depending on the desired properties of the produced material different monomers may be applied.

In order to introduce positive charges into the graft tentacles monomers from the following group can be selected:
2-(acryloylaminoethyl)trimethylammonium chloride,
3-(acryloylamino-propyl)trimethylammonium chloride,
2-(diethylaminoethyl)acrylamide,
2-(diethylaminoethyl)methacrylamide,
2-(dimethylaminoethyl)acrylamide,
2-(dimethylaminoethyl)methacrylamide,
3-(diethylaminopropyl)-acrylamide,
3-(diethylaminopropyl)methacrylamide,
3-(diethylamino-propyl)acrylamide,
3-(diethylaminopropyl)methacrylamide,
2-(meth-acryloylaminoethyl)trimethylammonium chloride,
3-(acryloylamino-propyl)trimethylammonium chloride,
N-(3-aminopropyl)methacrylamide hydrochloride,
[3-(Methacryloylamino)propyl]dimethyl(3-sulfopropyl)ammonium hydroxide inner salt,
2-(dimethylamino)ethyl methacrylate,
2-(diethylamino)ethyl methacrylate,
2-aminoethyl methacrylate hydrochloride,
2-(diisopropylamino)ethyl methacrylate, and
2-(tert-butylamino)ethyl methacrylate, By using monomers selected from the following group negative charges can be generated in the tentacles:
2-acrylamido-2-methylpropane-sulfonic acid,
2-Acrylamido-2-methyl-1-propanesulfonic acid sodium salt solution,
2-acrylamidoethanesulfonic acid,
carboxymethylacryl-amide; carboxyethylacrylamide,
carboxypropylacrylamide,
carboxy-methlymethacrylamide,
carboxyethylmethacrylamide,
carboxypropyl-methacrylamide,
acrylic acid,
methacrylic acid, and
3-Sulfopropyl methacrylate potassium salt.

By use of monomers selected from the following group on the other hand hydrophobic groups are introduced into the generated tentacles:
N-benzyl-2-methylacrylamide,
N-isopropylmethacrylamide,
N,N-dimethylmethacrylamide,
N,N-diethylmethacrylamide,
methyl methacrylate,
ethyl methacrylate,
hydroxyethyl methacrylate,
propyl methacrylate,
n-butyl methacyrlate,
isobutyl methacrylate,
sec-butyl methacrylate,
tert-butyl methacrylate,
hexyl methacrylate,
lauryl methacrylate,
isobornyl methacrylate,
benzyl methacrylate,
1-naphthyl methacrylate,
2-naphthyl methacrylate,
2-ethylhexyl methacrylate,
cyclohexyl methacrylate,
3,3,5-trimethylcyclohexyl methacrylate,
ferrocenylmethyl methacrylate, and
phenyl methacrylate The skilled person knows more suitable chemical compounds other than those listed here and that can serve as monomers in this context and which are suitable corresponding to bring positive or negative charges into the produced polymer chains.

Suitable fibers for the production of separation materials according to the present invention may be of any length and diameter and are preferably cut or staple fibers or a nonwoven fabric. They need not be bonded together as an integrated structure but can serve effectively as individual discrete entities. They may be in the form of a continuous length such as thread or monofilament of indeterminate length or they may be formed into shorter individual fibers such as by chopping fibrous materials (e.g., staple fibers) or as non-woven or woven fabrics, cutting the continuous length fiber into individual pieces, formed by a crystalline growth method and the like. Preferably the fibers are made of a thermoplastic polymer, such as polypropylene, polyester, polyethylene, polyamide, thermoplastic urethanes, polystyrenes, co-polyesters, or liquid crystalline polymers.

Fibers which are preferably used for the purpose described here, having a length which is much greater than the widest dimensions of the fiber cross-section, and which do not form a compact body. Preferably these fibers have a length in the range of some millimeters to several centimeters. For the purpose of the present invention, the fibers used have a length ranging from 0.5 mm to 5 cm, more suitable are corresponding fibers having a length ranging from 0.5 mm to 2.5 cm. Particularly well suited are fibers having a length in the range from about 0.5 mm to 2 mm.

In certain embodiments, the fiber has a cross-sectional length of from about 1 µm to about 100 µm and a cross-sectional width of from about 1 µm to about 100 µm. One suitable fiber has a cross-sectional length of about 20 µm and a cross-sectional width of about 10 µm. Preferably the fibers have a cross-sectional length of about 10-20 µm.

In certain embodiments, the fiber cross-section is generally winged-shaped, with a main body region defining a substantially longitudinal axis, and a plurality of projections extending radially outwardly from the main body region. The projections form an array of co-linear channels that extend along the length of the fiber, typically 20-30 such channels per fiber. In certain embodiments, the length of the projections is shorter than the length of the main body region. In certain embodiments, the fiber cross-section is generally winged-shaped, with a middle region comprising a longitudinal axis that runs down the center of the fiber and having a plurality of projections that extend from the middle region. In certain embodiments, a plurality of the projections extends generally radially from the middle region. As a result of this configuration, a plurality of channels is defined by the projections. Suitable channel widths between projections range from about 200 to about 1000 nanometers. Suitable fibers are disclosed in U.S. Patent Publication No. 2008/0105612, the disclosure of which is incorporated herein by reference.

Fibers with surface areas ranging from at least 1 m²/g to about 14 m²/g or even more are suitable. Furthermore, preferably suitable are fibers having a surface area of at least 20 m²/g, also more preferably a surface area of at least 25 m²/g, and also further preferably a surface area of at least 30 m²/g. This applies for winged fibers as well as for highly porous fibers. Thus, preferably fibers are used having surface areas in this range, but also fibers having much higher surface areas may be applied for the preparation of separation materials according to the invention.

Suitable fibers include porous fibers, such as those described in U.S. provisional application 62/044,630, the disclosure of which is incorporated herein by reference.

Porous fibers may have high surface areas, but it is essential that the pores are of sizes that allow to be functionalized by graft polymerization, whereby, however, the effectiveness and accessibility is not restricted in later separation processes. Furthermore, it is important that these porous fibers in application having necessary stability, so that they are suitable for use in compressed chromatography column.

In certain embodiments, the fibers can readily be packed under compression into a device or container with appropriate ports and dimensions so that no packing is required by the user as the product arrives ready for service. The fibers also can be used in a pre-formed bed format such as nonwoven sheetstock material created by a spunbond (continuous filament) or wet-laid (cut fiber) process, common in the nonwovens industry. Suitable preformed fiber formats include sheets, mats, webs, monoliths, etc.

The shaped fiber media offers certain advantages over porous chromatographic beads by nature of its morphology. Typically in bead-based chromatography, the rate limiting step in the separation process is penetration of the adsorbate (solute) into the depths of porous beads as controlled by diffusion; for macromolecules such as proteins, this diffusional transport can be relatively slow. For the high surface area fibers disclosed herein, the binding sites are mainly exposed on the exterior of the fibers and therefore are easily accessed by adsorbate molecules in the flow stream. The rapid transport offered by this approach allows for short residence time (high flow velocity), thereby enabling rapid cycling of the media by means such as simulated moving bed systems. As speed of processing is a critical parameter in the production of biologies, fiber-based chromatographic media as described herein has particular process advantages over conventional bead-based media.

A suitable column packing density of between about 0.1-0.4 g/ml, preferably about 0.32 g/ml, at a bed height of 1-5 cm will provide sufficient flow uniformity for acceptable performance in a chromatographic evaluation. The surface functionalized fiber media of the embodiments disclosed herein show a high permeability in a packed bed format.

A particular advantage of this new surface functionalized fiber media described here, is its versatility. Depending on the used fibers and on their derivatization, separation and purification of a variety of target molecules is possible, for example proteins, especially protein A, peptides, lipids, DNA molecule, RNA molecule, organic molecules, inorganic molecule, cells, viruses, bacteria, toxins or a prion. Especially in separation processes that are applied to biological fluids, the properties of the materials described herein prove to be particularly advantageous and effective.

ABBREVIATIONS

AEX anion-exchange chromatography media
aq. aqueous
ArlS-ArlR two-component system, which is a regulator of virulence gene expression in *Staphylococcus aureus*
CEX cation-exchange chromatography media
CHO Chinese Hamster Ovary
CV column volume
DI deionized water
DNA deoxyribonucleic acid
DSP downstream process
Fab fragment antigen-binding (Fab fragment) is a region on an antibody that binds to antigens
Fc region (Fragment, crystallizable) region, which is composed of two heavy chains that contribute two or three constant domains depending on the class of the antibody
GMA glycidyl methacrylate
HCP host cell protein
HIC hydrophobic interaction chromatography
IgG Immunoglobulin G (IgG), or gamma globulin, the antibodies (immunoglobulins) of class G,
LRV "log removal value" The term refers to the log (base 10) of the ratio of the mass of impurity in the load of a purification step to the mass of impurity in the product pool.
mAb monomclonal antibody
Q-functionalization surface functionalization with quaternary ammonium (Q)

TABLES

Table 1: Characteristics of columns packed with either AEX fibers, CEX fibers or a blend of both AEX and CEX fibers in view of bed depth and column volume, pressure and flowrate, permeability and velocity.

Table 2: Flow-through purification data for mAb04 using AEX fiber media, CEX fiber media and blended AEX/CEX fiber media columns in view of the characteristics, flow through, loading of mAb on fibers, recovery of mAb, HCP concentration and LRV of HCP.

The present description enables the person skilled in the art to apply the invention comprehensively. Even without further comments, it is therefore assumed that a person skilled in the art will be able to utilise the above description in the broadest scope.

If anything is unclear, it goes without saying that the publications and patent literature cited should be consulted. Accordingly, these documents are regarded as part of the disclosure content of the present description.

For better understanding and in order to illustrate the invention, examples are given below which are within the scope of protection of the present invention. These examples also serve to illustrate possible variants. Owing to the general validity of the inventive principle described, however, the examples are not suitable for reducing the scope of protection of the present application to these alone.

Furthermore, it goes without saying to the person skilled in the art that, both in the examples given and also in the remainder of the description, the component amounts present in the compositions always only add up to 100% by weight or mol %, based on the composition as a whole, and cannot exceed this, even if higher values could arise from the percent ranges indicated. Unless indicated otherwise, % data are % by weight or mol %, with the exception of ratios, which are shown in volume data, such as, for example, eluents, for the preparation of which solvents in certain volume ratios are used in a mixture.

The temperatures given in the examples and the description as well as in the claims are always in ° C.

EXAMPLES

Example 1

Graft Polymerization of Un-Modified Nylon Fibers 10 g Allasso nylon fibers and water (466 ml) are added into a 500 ml bottle. 14 ml 1 M $HNO_3$ (14.4 mmol) are added to the reaction mixture, followed by the addition of 1.2 ml of a 0.4 M ammonium cerium(IV) nitrate solution in 1 M $HNO_3$ (0.480 mmol). The reaction mixture is agitated for 15 minutes. 3.39 g Glycidyl methacrylate (GMA, 24 mmol) are added. Now the agitated reaction mixture is heated to 35° C. for 1 hour. After cooling down to room temperature, the solids are washed with DI water (3×300 ml) and the damp material is used immediately in the following step.

Example 2

Q-Functionalization of Epoxy-Functionalized Fibers (AEX Fiber Media)

The damp GMA functionalized fibers from example 1 are added into a 2 L bottle together with water (500 ml) and a solution of 50 wt % trimethylamine (aq.) in methanol (500 ml). The mixture is agitated for 18 hours at room temperature. Then the fiber solids are subsequently washed with a solution of 0.2 M ascorbic acid in 0.5 M sulphuric acid (3×400 ml), DI water (3×400 ml), 1 M sodium hydroxide solution (3×400 ml), DI water (3×400 ml) and ethanol (1×400 ml). Subsequently, the material is placed in an oven to dry at 40° C. for 48 hours.

Yield: 11.74 g of a white fibrous solid

Example 3

Graft Polymerization of Un-Modified Nylon Fibers (CEX Fiber Media)

10 g Allasso nylon fibers and water (460 ml) are added into a 1000 ml bottle. 29.8 ml 1 M $HNO_3$ solution (30 mmol) are added to the reaction mixture, followed by the addition of a solution 7.46 ml of a 0.4 M ammonium cerium(IV) nitrate solution in 1 M $HNO_3$ (3.00 mmol). The reaction mixture is agitated for 15 minutes. Then 61.5 g 3-sulfopropylmethacrylate potassium salt (3-SPMA, 250 mmol) are added and the resulting agitated reaction mixture is heated to 35° C. for 18 hours. After cooling to room temperature, the fiber solids from each bottle are washed with DI water (3×300 ml), 0.2 M ascorbic acid in 0.5 M sulphuric acid (3×300 ml), DI water (3×300 ml), 1 M sodium hydroxide solution (3×300 ml), DI water 3×300 ml) and ethanol (1×300 ml). The prepared material is then placed in an oven to dry at 40° C.

Yield: 11.38 g of a white fibrous solid

Example 4

Blended Ion-Exchange Media Column Packing 0.35 g of a slurry of the described fiber media (see Table 1) in 25 mM Tris pH 8 is added into a 6.6 mm ID Omnifit column. The fiber media is compressed to a bed depth of 3.0 cm (1.03 ml column volume, 0.35 g/ml fiber packing density). Fiber bed permeability is assessed by flowing 25 mM Tris pH 8 buffer through the column at a flow rate of 2.0 ml/min and measuring the column pressure drop by means of an electric pressure transducer. Fiber bed permeability values are also provided in Table 1.

TABLE 1

Characteristics of columns packed with either AEX fibers, CEX fibers or a blend of both AEX and CEX fibers

| Column type | Media type, amount [g] | Bed depth, [cm] CV [ml] | Pressure, [PSI flowrate [ml/min] | Permeability [mDarcy] velocity [cm/h] |
|---|---|---|---|---|
| AEX column | AEX fibers, example 2 0.35 g | 3.0 cm, 1.03 ml | 23.5 PSI 2.0 ml/min | 185 mDa, 350 cm/h |
| CEX column | CEX fibers, example 3, 0.35 g | 3.0 cm, 1.03 ml | 20.0 PSI 2.5 ml/min | 269 mDa, 440 cm/h |
| AEX and CEX blended column | AEX fibers, example 2, 0.18 g CEX fibers, example 3, 0.18 g | 3.0 cm, 1.03 ml | 28.0 PSI 1.9 ml/min | 144 mDa 330 cm/h |

Example 5

Comparison of HCP Removal from mAb04 Protein a Elution with AEX Fiber, CEX Fiber, and a Blend of Both AEX and CEX Media A cell culture of mAb04 was clarified and then captured at a concentration of 7.2, mg/ml using Protein A column chromatography. The pH of the mAb04 Protein A elution was then adjusted to pH 5 with Tris base for storage and then filtered through a Stericup-GP 0.22 µm Millipore ExpressPLUS membrane (1 L, catalogue number: SCGPU02RE, Millipore Corp. Billerica, Mass., 01821, USA). The pH of the solution was adjusted to pH 7.0 with Tris base just prior to use. The resulting solution was then filtered through a Stericup-GP 0.22 mm Millipore Express PLUS membrane (1 L, catalogue number SCGPU02RE, Millipore Corp. Billerica, Mass., 01821, USA).

Three columns containing functionalized fibers were prepared as described in example 4. The first 1 ml column consisted of AEX fibers functionalized with quaternary ammonium ligands from example 2 (lot ID #JA7654-163B). The second 1 ml column consisted of CEX fibers functionalized with sulfonate ligands from example 3 (lot ID #JA7654-131). The third 1 ml column consisted of a blend of equal quantities of AEX fibers functionalized with quarternary ammonium ligands from example 2 (JA7654-163B) and CEX fibers functionalized with sulfonate ligands from example 3 (JA7654-131), see example 4. The three columns are equilibrated with a buffer solution (25 mM Tris at pH 7).

120 ml of a Protein A elution pool is passed through each column at a flow rate of 0.33 ml/min giving a residence time of 3 min in each fiber packed column. Three 40 ml fractions are collected from each column. Pooled samples representing the elution pool composition after 80 ml and 120 ml, which have passed through the column, are submitted for analysis. The solutions are analyzed for host cell protein (HCP) and IgG concentration. HCP analysis is performed using a commercially available ELISA kit from Cygnus Technologies, Southport, N.C., USA, catalogue number F550, following kit manufacturer's protocol. IgG concentration is measured using an Agilent HPLC system equipped with a Poros® A Protein A analytical column. Results are summarized in Table 3 and FIG. 3.

The results of the experiment show that combining the mixed bed column containing the AEX and CEX fiber gave greater HCP removal with a log removal value (LRV) of approximately 1.6 LRV. This greatly exceeds the approximately 0.9 LRV of HCP observed for the column containing only the AEX fibers and the approximately 0.6 LRV of HCP observed for the column that contained only the CEX fibers. The greater amount of HCP removed by the column with a blend of both fibers is likely due to the fact that it has two different ligands which are able to adsorb HCP with different characteristics. The AEX functionalized fibers are able to bind to impurities that have negatively charged regions on their surfaces, which is typical for proteins with lower isoelectric points. The CEX functionalized fibers are able to bind impurities that have positively charged regions on their surface, which is typical of proteins with higher isoelectric points.

TABLE 2

Flow-through purification data for mAb04 using AEX fiber media, CEX fiber media and blended AEX/CEX fiber media columns

| Flow through train | Loading of mAb on fibers [kg/l] | mAb [g/l] | mAb recovery | HCP [ng/ml] | HCP [ppm] | LRV of HCP |
|---|---|---|---|---|---|---|
| untreated | — | 7.20 | — | 1876 | 261 | — |
| AEX fibers | 0.54 | 7.15 | 99% | 223 | 31 | 0.92 |
| AEX fibers | 0.82 | 7.16 | 99% | 242 | 34 | 0.89 |
| CEX fibers | 0.54 | 6.67 | 93% | 476 | 71 | 0.57 |
| CEX fibers | 0.82 | 6.82 | 95% | 494 | 72 | 0.56 |
| blend of AEX and CEX fibers | 0.54 | 6.97 | 97% | 38 | 5 | 1.68 |
| blend of AEX and CEX fibers | 0.82 | 7.03 | 98% | 47 | 7 | 1.59 |

Figure 3:
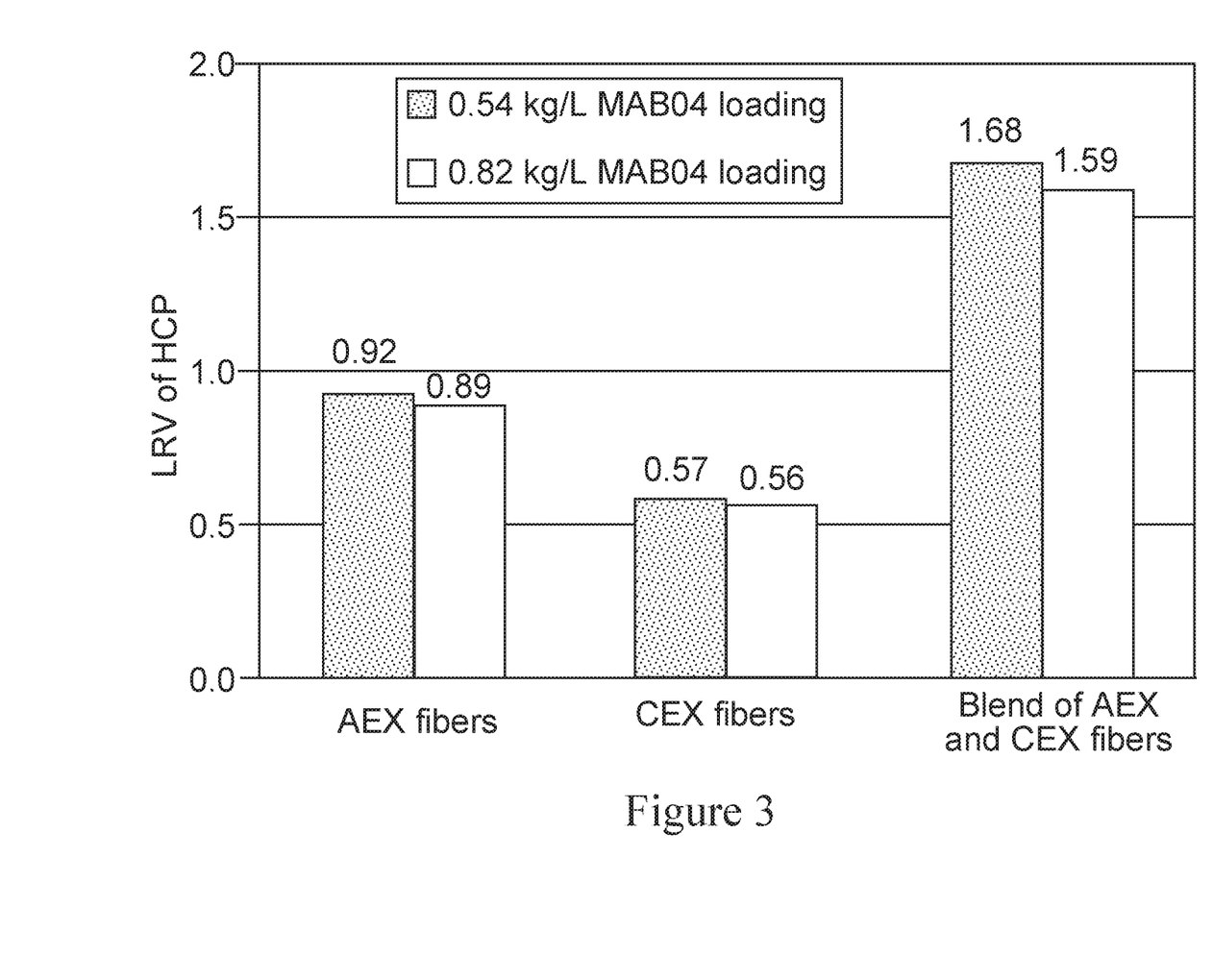
FIG. 3: shows HCP clearance from the mAb04 Protein A feed after flow through purification in the form of bar charts, where the described media from example 5 are used (AEX fiber, CEX fiber, and a blend of both AEX and CEX media).

FIG. 3: shows HCP clearance from the mAb04 Protein A feed after flow through purification using the described media from example 5.

Example 6

Fiber Media with Hydrophobic Interaction Chromatography Ligand

The hydrophobic interaction chromatography media described in the text above can be prepared by using the fiber surface modification procedures described in examples 1 and 3 and a methacrylate monomer or other polymerizable functionality selected from a group comprising
methyl methacrylate,
(hydroxyethylmethacrylate,
poly(propyleneglycol)monomethacrylate,
(phenyl)methacrylate,
((n-butyl)methacrylate,
(n-hexyl)methacrylate).

The ceric ion redox polymerization procedure described in examples 1 and 3 can be used to directly modify the surface of the Allasso nylon fiber media with reactive methacrylic monomers disclosed in this example. (see FIG. 4) After grafting polymerization and suitable washing procedures (also described in examples 1 and 3), the fiber media now displays an appropriate hydrophobic ligand functionality for hydrophobic interaction chromatography (HIC). The media is now ready to be loaded into a chromatography column or other device for the tandem chromatography application described in the text above.

Figure 4:
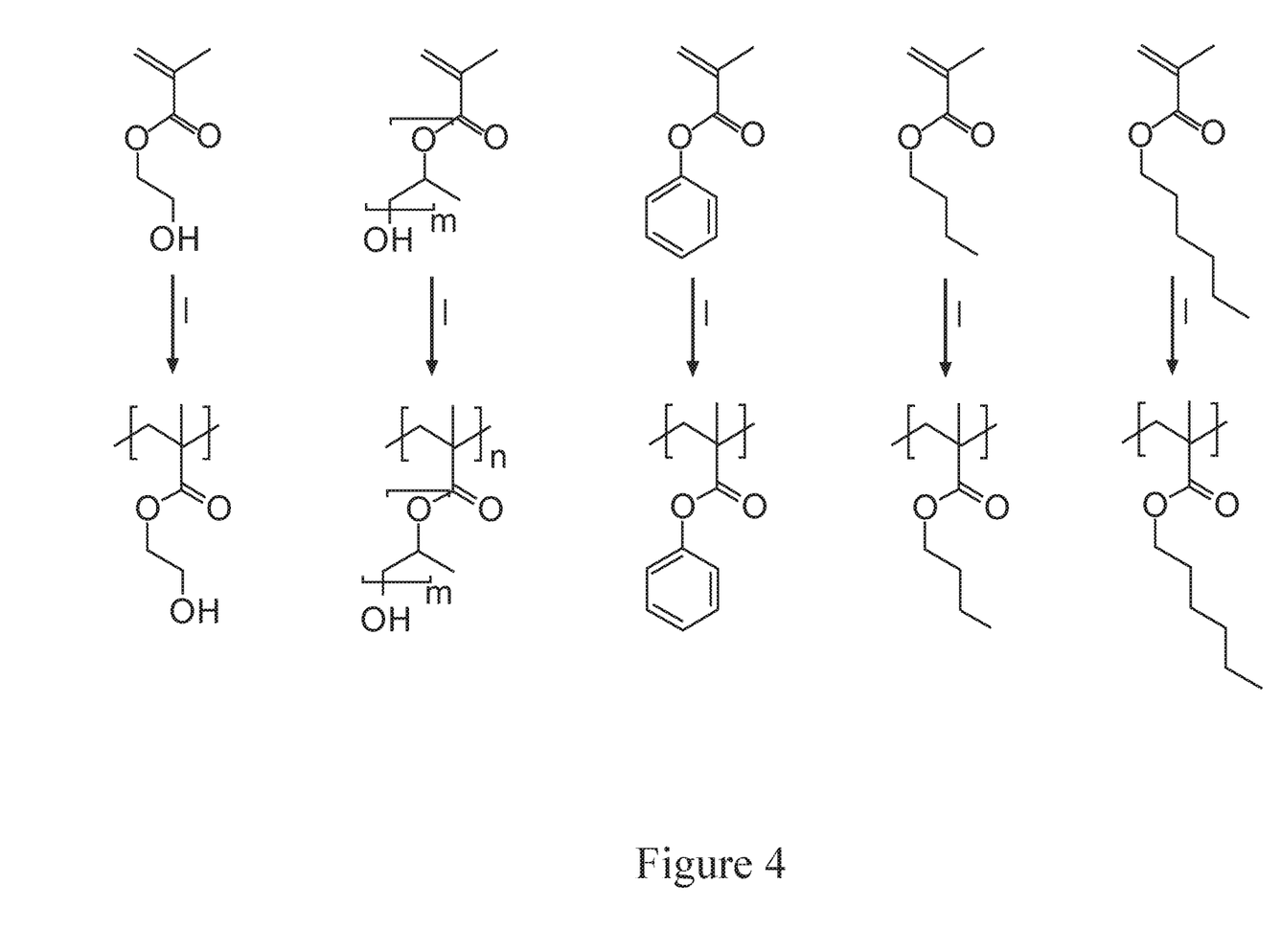
FIG. 4: Modified surface of the winged nylon fiber media with a selection of reactive methacrylic monomers ((hydroxyethyl)methacrylate, poly(propyleneglycol)-monoethacrylate, (phenyl)methacrylate, (n-butyl)methacrylate, (n-hexyl)methacrylate)) in presence of 0.4 M cerium(IV) ammonium nitrate.

FIG. 4: Selection of HIC ligands suitable for fiber media of the present invention and process for attachment to the surface of the Allasso nylon fiber media.

i: Allasso fiber media surface modification using a methacrylate monomer selected from the group comprising: (hydroxyethyl)methacrylate, poly(propyleneglycol)monoethacrylate,
(phenyl)methacrylate, (n-butyl)methacrylate, (n-hexyl) methacrylate), Allasso nylon fiber, 0.4 M cerium(IV) ammonium nitrate, nitric acid, water 35° C., 18 hrs according to the surface modification procedure employed in examples 1 and 3.

Example 7

Fiber Media Modified with Poly(Hydroxyethylmethacrylate) Ligand for Hydrophobic Interaction Chromatography Hydroxyethylmethacrylate (HEMA, 1.69 g, 13 mmol) and water (232.5 ml) are added into a 500 ml bottle. Then 5.00 g of Allasso nylon fibers (Winged Fiber™), are added to this solution. 1 M $HNO_3$ solution (7.21 ml, 7.2 mmol) are added to this reaction mixture, followed by the addition of a 0.4 M solution of ammonium cerium(IV) nitrate in 1 M $HNO_3$ (0,601 ml, 0,240 mmol). The reaction mixture is heated to 35° C. for 1 hour. After cooling to room temperature, the solids are washed with a solution of 0.2 M ascorbic acid in 0.5 M sulphuric acid (3×100 ml), DI water (3×100 ml) 1 M sodium hydroxide solution (3×100 ml) DI water (3×100 ml) and ethanol (1×100 ml). The material is placed in an oven to dry at 40° C. for 12 hours.

Yield: 5.58 g as a white fibrous solid.

What is claimed:

1. A single housing comprising a packed bed of fibers for purification of biomolecules, said packed bed having a blend of a first chromatography media and a second chromatography media, said first chromatography media comprising fibers having surface pendant functional groups enabling anion-exchange chromatography, and said second chromatography media comprising fibers having surface pendant functional groups enabling cation-exchange or hydrophobic interaction chromatography, or said first chromatography media comprising fibers having surface pendant functional groups enabling cation-exchange chromatography, and said second chromatography media comprising fibers having surface pendant functional groups enabling hydrophobic interaction chromatography.

2. The single housing of claim 1, wherein said first chromatography media comprises fibers having surface pendant functional groups enabling anion-exchange chromatography, and said second chromatography media comprises fibers having surface pendant functional groups enabling cation-exchange chromatography.

3. The single housing of claim 1, wherein said first chromatography media comprises fibers having surface pendant functional groups enabling anion-exchange chromatography, and said second chromatography media comprises fibers having surface pendant functional groups enabling hydrophobic interaction chromatography.

4. The single housing of claim 1, wherein said first chromatography media comprises fibers having surface pendant functional groups enabling cation-exchange chromatography, and said second chromatography media comprising fibers having surface pendant functional groups enabling hydrophobic interaction chromatography.

5. The single housing of claim 1, wherein the fibers in said first chromatography media are derivatized by adding surface pendant functional groups enabling anion-exchange chromatography, and wherein the fibers in said second chromatography media are derivatized by adding surface pendant functional groups that enable hydrophobic interaction chromatography.

\* \* \* \* \*